United States Patent [19]

Heck

[11] 4,175,187

[45] Nov. 20, 1979

[54] PROCESS FOR THE PREPARATION OF TERTIARY ALLYLIC AMINES FROM VINYLIC HALIDES AND OLEFINS

[75] Inventor: Richard F. Heck, Wilmington, Del.

[73] Assignee: University of Delaware, Newark, Del.

[21] Appl. No.: 954,184

[22] Filed: Oct. 24, 1978

[51] Int. Cl.$^2$ .................................. C07D 295/02
[52] U.S. Cl. ............................ 544/170; 544/178; 546/184; 546/192; 546/248; 260/326.8; 260/583 H; 260/593 R; 260/654 R; 260/345.9 R; 560/205; 560/207; 568/596; 585/359; 585/600; 585/605; 585/612
[58] Field of Search ............... 544/178, 170; 546/184, 546/192, 248; 260/326.8, 583 H

[56] References Cited

U.S. PATENT DOCUMENTS

| | | | |
|---|---|---|---|
| 3,417,130 | 12/1968 | Pruett et al. | 260/583 H |
| 4,083,874 | 4/1978 | McConaghy et al. | 260/583 H |
| 4,100,194 | 7/1978 | Hobbs et al. | 260/583 H |

*Primary Examiner*—Alan L. Rotman
*Assistant Examiner*—R. W. Ramsuer

[57] ABSTRACT

Tertiary allylic amines are obtained from vinylic halides and olefins, and substituted derivatives thereof, by reacting said halide with a mono-, di-, or tri-substituted olefin and an unhindered basic secondary amine in the presence of a palladium catalyst.

8 Claims, No Drawings

PROCESS FOR THE PREPARATION OF TERTIARY ALLYLIC AMINES FROM VINYLIC HALIDES AND OLEFINS

This invention relates to a catalytic process for the preparation of tertiary allylic amines from vinylic halides, and substituted derivatives thereof, by reacting said halide with a mono-, di-, or tri-substituted olefin and an unhindered basic secondary amine in the presence of a palladium catalyst.

The Government has rights in this invention pursuant to Grant No. CHE-04973 AO1 awarded by the National Science Foundation.

It is known that rhodium chloride will catalyze the addition of dialkylamines to conjugated dienes (e.g., D. Rose, Tetrahedron Letters, p. 2776 (1972)). This reaction is limited by the difficulty of obtaining conjugated dienes, and also by the fact that isomeric mixtures are formed. In addition, the reaction employs the very rare and expensive metal rhodium as a catalyst.

It is an object of this invention to produce catalytically allylic amines under mild conditions in a highly selective manner from readily available vinylic halides and olefins.

In accordance with this invention, it has been found that tertiary allylic amines are produced when vinylic halides, or substituted derivatives thereof, are contacted with mono-, di-, or tri-substituted olefins and an unhindered basic secondary amine in the presence of a palladium catalyst.

The process of this invention appears to depend upon the reactions broadly expressed as follows:

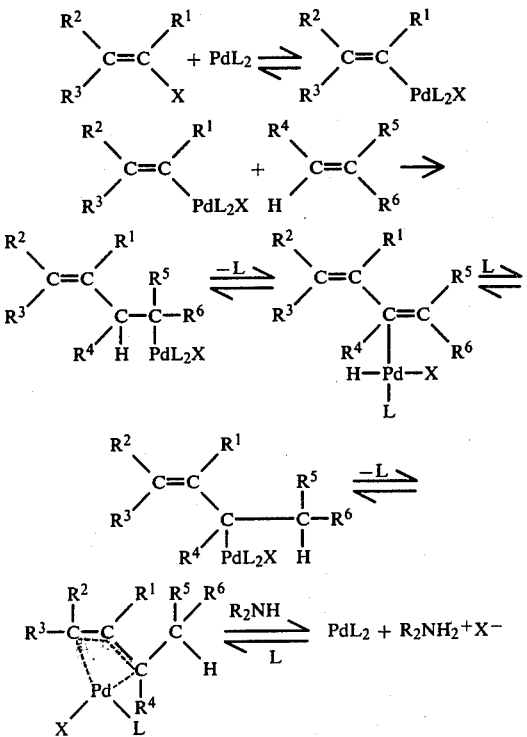

-continued

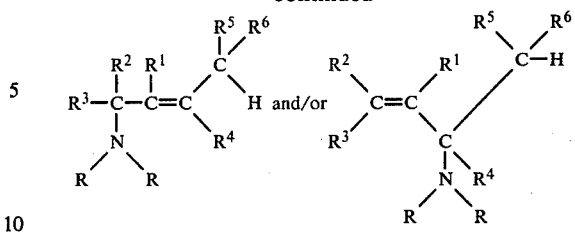

in which the R, $R^1$, $R^2$, $R^3$, $R^4$, $R^5$ and $R^6$ groups may be hydrogen, alkyl, aryl or heteroaryl groups or substituted derivatives thereof with up to about 30 carbons. The X group is iodide, bromide, or chloride and L is a triarylphosphine or a basic, unhindered secondary amine. The R groups may be methyl, ethyl or be part of a ring system involving both R groups in the $R_2NH$. The $R^1$, $R^2$ and $R^3$ as well as the $R^4$, $R^5$ and $R^6$ groups also may be part of ring systems. These $R^1$–$R^6$ groups may also have various substituents present such as alkyl and aryl groups, cycloalkyl groups, nitro, cyano, ester, carboxylate, amide, aldehyde, hydroxyl, ether, amino or even halogen groups if these groups are less reactive than the other groups in the reactants which are intended to take part in the reaction.

Examples of vinylic halides, $R^2R^3C=CR^1X$, which will undergo the reaction of this invention are vinyl bromide, vinyl iodide, vinyl chloride, 1-bromo-1-propene, 2-bromopropene, 2-chloropropene, 1-bromo-2-methyl-1-propene, 1-bromo-1-hexene, 1-bromo-1-butene, 1-iodo-2-methyl-1-propene, methyl 2-methyl-3-bromopropenoate, β-bromostyrene, 3-bromoacrolein dimethyl acetal, and 1-bromocyclopentane.

The olefinic reactant normally will react best if only two of the R groups are carbon groups and the other two are hydrogen. Examples of olefins which are useful include ethylene, propylene, butene, cyclohexene, 1-hexene, isobutylene, acrolein dimethyl acetal, allyl alcohol, allyl pyranyl ether, allylbenzene, butadiene, isoprene, vinyl methyl ether, methallyl pyranyl ether, vinylbenzonitrile, vinylpyridine, vinylnaphthalene, 9-decen-1-ol, 5-dimethylamino-1-hexene and methallyl alcohol.

Examples of basic, unhindered secondary amines which can be used in this process are dimethylamine, diethylamine, piperidine, morpholine, pyrrolidine, 4-methylpiperidine, benzylmethylamine, piperazine, and monomethylpiperazine.

The coordinating group, L, may be a basic, unhindered secondary amine as listed in the previous paragraph, or a triarylphosphine such as triphenylphosphine, tri-p-anisylphosphine, tri-o-tolylphosphine, tri-p-tolylphosphine, tri-p-fluorophenylphosphine, and tri-o-ethylphenylphosphine.

The process of this reaction is carried out at a temperature in the range of 20° to about 175° C., with about 50°–150° C. being preferred, and within a pressure range of about 0.5 to about 50 atmospheres.

Generally no solvent other than the reactants is necessary for the reaction, provided that they are liquids at the reaction temperature or at least if the solids used are partially soluble in the other liquid reactants. Solvents such as excess reactant secondary amine, methanol, ethanol, isopropanol, tetrhydrofuran, toluene, N-methylpyrrolidone, dimethylformamide, acetonitritile and N,N-dimethylacetamide may be used, however, with little effect upon the reaction.

The ratios of reactants used are not critical. Generally two or more equivalents of secondary amine are used per mole of vinylic halide, although the normal products are also obtained with smaller amounts, but often in reduced yields and at reduced rates. The vinylic halide is normally the limiting reactant, and the olefin is used in at least equivalent amounts.

Catalyst concentrations of from about 0.001 mole percent to about 10 mole percent of the vinylic halide or more may be used with about 0.01 to 2% being generally preferred. The catalyst may be added as finely divided palladium metal in cases where the vinylic halide is an iodide, but in other cases palladium(II) salts are preferred, such as the dihalides or diacetates. If triarylphosphines are used in conjunction with the palladium salt the phosphine may be added separately or in the form of a complex with the palladium(II) salt. A ratio of two triarylphosphine molecules to each palladium(II) salt molecule is usually sufficient, although larger amounts are not harmful and, in fact, may be helpful in some instances.

It should be noted that the process of this invention does not involve the formation of conjugated dienes initially, followed by a palladium-catalyzed addition of the secondary amine to the diene. It has been shown that conjugated dienes, while present in these reaction mixtures as by-products, do not undergo further reaction with the secondary amines present in the reaction mixture, since the ratios of amine products to conjugated dienes remain constant throughout the reactions.

The tertiary allylic amines are valuable chemical intermediates. They can be converted to allylic bromides by reaction with cyanogen bromide or directly into alcohols by reaction with hydrogen peroxide, followed by rearrangement by heating and then reduction. Terpenes of value in the perfume industry and insect pheromones of value in insect control, for example, can be advantageously prepared by means of this process.

The following examples illustrate various ramifications of this invention, but the invention is not limited thereby.

EXAMPLE 1

A mixture of 10 mmoles of vinyl bromide, 30 mmoles morpholine, 12.5 mmoles 1-hexene, 0.10 mmole palladium acetate and 0.20 mmole of tri-o-tolyphosphine was heated in a capped bottle at 100° C. for 18 hrs. The reaction mixture was cooled, diluted with water and ether and the ether layer was separated. This layer was washed with water, dried over anhydrous magnesium sulfate and distilled under reduced pressure. There was obtained a 10% yield of two octadiene isomers and 48% N-oct-2-enylmorpholine, b.p. 94° C. (1.2 mm.)

EXAMPLE 2

A mixture of 10 mmoles cis-1-bromo-1-hexene, 30 mmoles morpholine, 4 ml of acetonitrile, 0.10 mmole palladium acetate and 0.20 mmole of tri-o-tolylphosphine was heated in a pressure vessel under 200 psig of ethylene at 100° C. for 2 hrs. After cooling, the pressure was released and the reaction products were isolated as in Example 1. There was obtained about 5% cis-1,3-octadiene, 84% N-oct-3-en-2-ylmorpholine and 8% N-oct-2-en-4-ylmorpholine.

EXAMPLE 3

A reaction was carried out as in Example 1 employing trans-1-bromo-1-propene instead of vinyl bromide. After 47 hrs. at 100° C. the products were isolated and found to be 40% nonadiene isomers, 40% N-non-3-en-2-ylmorpholine and 5% N-(4-methyloct-3-en-2-yl)morpholine.

EXAMPLE 4

A reaction was carried out as in Example 1 employing cis-1-bromo-1-propene instead of vinyl bromide. After 40 hrs. of reaction at 100° C. there was isolated 35% nonadienes, 50% N-non-3-en-2-ylmorpholine and 5% N-(4-methyloct-3-en-2-yl) morpholine.

EXAMPLE 5

A reaction was carried out as in Example 1 employing 1-bromo-2-methyl-1-propane instead of vinyl bromide. After 48 hrs. at 100° C. the products were isolated. There was obtained a 58% yield of a mixture of six decadienes and 31% of N-(2-methylnon-3-ene-2-yl)morpholine.

EXAMPLE 6

The process of Example 5 was carried out with piperidine instead of morpholine. After 48 hrs. at 100° C., the products consisted of 56% of a mixture of six decadienes and 40% of N-(2-methylnon-3-en-2-yl)piperidine.

EXAMPLE 7

Example 1 was carried out with 2-bromopropene in place of vinyl bromide. After 68 hrs. at 100° C. there was produced a 32% yield of a mixture of 2-methyl-1,3- and 2-methyl-1,4-octadienes and 64% N-methyloct-2-en-2-ylmorpholine.

EXAMPLE 8

A mixture of 10 mmoles 2-bromopropene, 12.5 mmoles 2-methyl-3-buten-2-ol, 30 mmoles piperidine, 0.10 mmole palladium acetate and 0.20 mmole triphenylphosphine were heated together at 100° C. for 20 hrs. From the reaction mixture there was isolated an 80% yield of 2,5-dimethyl-6-piperidinohex-4-en-2-ol.

EXAMPLE 9

A mixture of 10 mmoles cis-1-bromo-1-propene, 12.5 mmoles acrolein dimethyl acetal, 30 mmoles piperidine and 0.10 mmole palladium acetate was heated at 100° C. for 6 hours. After cooling the products were separated and found to be 17% trans, cis-sorbyl aldehyde dimethyl acetal and 66% 5-piperidino-3-hexenal dimethyl acetal.

EXAMPLE 10

The process of Example 9 when carried out with 10 mmoles trans-1-bromo-1-propene gives trans,trans-sorbyl aldehyde dimethyl acetal and 5-piperidino-3-hexenal dimethyl acetal in about the same yields as from the cis-1-bromo-1-propene.

EXAMPLE 11

A mixture of 10 mmoles 2-bromopropene, 12.5 mmoles 3-buten-2-ol, 30 mmoles piperidine, 0.20 mmole palladium acetate and 0.40 mmole tri-o-tolylphosphine was heated at 100° C. for 2 hrs. Analysis of the reaction mixture by gas chromatography showed that about 30% of 5-methyl-5-hexen-2-one and 70% 5-methyl-6-piperidino-4-hexen-2-ol had been formed.

EXAMPLE 12

The process of Example 11 was repeated employing 12.5 mmoles 1-buten-3-yl dihydropyranyl ether in place of 1-buten-3-ol. After 44 hrs. of reaction at 100° C. there was obtained 63% of the tetrahydropyranyl ether of 5-methyl-3,5-hexadien-2-ol and 28% of 5-methyl-6-piperidino-4-hexen-2-ol.

EXAMPLE 13

A mixture of 10 mmoles 2-methyl-1-bromo-1-propene, 12.5 mmoles 2-methyl-3-buten-2-ol, 30 mmoles piperidine, 0.20 mmole palladium acetate and 0.40 mmole triphenylphosphine was reacted at 100° C. There was produced 61% of a mixture of nonadienols, 31% 2,6-dimethyl-6-piperidino-4-hepten-2-ol and 6% of what is believed to be 2,6-dimethyl-4-piperidino-5-hepten-2-ol.

EXAMPLE 14

The process of Example 1 was carried out with vinyl chloride instead of vinyl bromide and N-oct-2-enylmorpholine was obtained as a product.

EXAMPLE 15

The process of Example 1 was carried out with 2-methyl-1-iodo-1-propene instead of with vinyl bromide and N-(2-methylnon-3-en-2-yl)morpholine was obtained.

EXAMPLE 16

The process of Example 2 was carried out with diethylamine instead of morpholine and 2-diethylamino-3-octene was obtained in 80% yield.

EXAMPLE 17

The process of Example 1 was carried out with pyrrolidine instead of morpholine and N-oct-2-enylpyrrolidine was obtained.

As can be seen from the above examples, this invention is broadly applicable to a wide variety of vinylic halides. The products are valuable chemical intermediates as hereinbefore noted. This invention provides a new method for producing complex molecules from simpler ones and is generally very easy to use. The catalyst is not only highly effective but also is non-volatile and presents no health hazard to use.

The term "substituted ethylene", as used in the claims, is intended to include also dienes, both conjugated and non-conjugated. Thus, the following examples of the practice of this invention pertain to dienes of both of the aforesaid types.

EXAMPLE 18

Here an isolated type diene, namely, 1,7-octadiene, was reacted with morpholine to form an amine in accordance with the schematic reaction

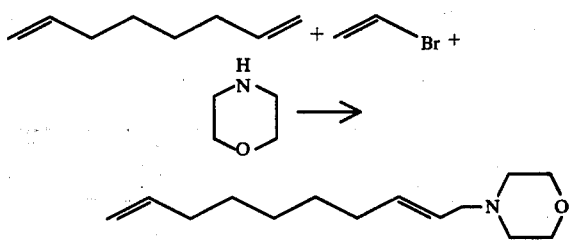

The conditions were:

A mixture of 44 ml (300 mmoles) 1,7-octadiene, 7.1 ml (100 mmoles) vinyl bromide, 22 ml (250 mmoles) morpholine, 0.224 g (1.0 mmole) palladium acetate and 0.608 g (2.0 mmoles) tri-o-tolylphosphine was heated in a capped bottle at 100° for 22 hrs. After cooling the reaction mixture was diluted with aqueous sodium hydroxide and the product was extracted with three portions of ether. The extracts were dried over anhydrous magnesium sulfate and distilled. There was obtained 15.04 g (68%) of 1-mropholino-2,9-decadiene, b.p. 104°–7° at 0.9 mm.

This product was converted into 1-chloro-2,9-decadiene by reaction with excess methyl chloroformate in 80% yield.

The following tabulated Examples 19-29, both inclusive, utilized a variety of vinylic halides in Pd-catalyzed reaction with a number of specific conjugated dienes, together with one of the secondary amines morpholine (abbrev. HM) and piperidine (abbrev. HP).

Table I

| | Vinylation Reactions of Conjugated Dienes at 100° C.[a] | | | | | |
|---|---|---|---|---|---|---|
| Example | Vinylic Halide | Diene | Amine[b] | Phosphine | Time, hrs. | Products, % Yield |
| 19 | Vinyl bromide[c] | E-1,3-pentadiene[c] | HM | P(o-tol)$_3$ | 17 | 6-morpholino-1,4-heptadiene, 52% |
| 20 | Z-1-Bromopropene | isoprene | HM | P(o-tol)$_3$ | 5 days | 2-methyl-1-morpholino-2,5-heptadiene, 40% |
| 21 | 2-Bromopropene | 1,3-butadiene | HP | — | 30 | 2-methyl-6-piperidino-1,4-hexadiene, 60% |
| 22 | 2-Bromopropene | isoprene | HM | P(o-tol)$_3$ | 45 | 2,5-dimethyl-1-morpholino-2,5-hexadiene, 40% |
| 23 | 2-Bromopropene | E-1,3-pentadiene | HM | P(o-tol)$_3$ | 30 | 2-methyl-6-morpholino-1,4-heptadiene, 55% |
| 24 | 2-Bromopropene | 4-methyl-1,3-pentadiene | HM | P(o-tol)$_3$[d] | 22 | 2,6-dimethyl-1,3,5-heptatriene, 12%  2,6-dimethyl-1-morpholino-2,5-heptadiene, 3%  2,6-dimethyl-6-morpholino-1,4-heptadiene, 26% |
| 25 | 2-Bromopropene | 1,3-cyclohexadiene | HP | — | 24 | 1-isopropenyl-1,3-cyclohexadiene, 21%  3-piperidino-6-isopropenylcyclohexene, 35%  3-piperidino-4-isopropenylcyclohexene, 15% |
| 26 | 2-Bromopropene | 1-methyl-1,3-cyclohexadiene | HP | — | 20 | 1-isopropenyl-4-methyl-1,3-cyclohexadiene, 39% |

Table I-continued

Vinylation Reactions of Conjugated Dienes at 100° C.[a]

| Example | Vinylic Halide | Diene | Amine[b] | Phosphine | Time, hrs. | Products, % Yield |
|---|---|---|---|---|---|---|
| 27 | 2-Bromopropene | 1-methyl-1,3-cyclohexadiene | HP | P(o-tol)$_3$ | 60 | Unidentified triene, 13%<br>4-isopropenyl-1-methyl-3-piperidinocyclohexene, 9%<br>1-isopropenyl-4-methyl-1,3-cyclohexatriene, 22% |
| 28 | Z-3-Iodo-3-hexene | E-1,3-pentadiene | HM | P(o-tol)$_3$ | 13 | Unidentified triene, 29%<br>4-isopropenyl-1-methyl-3-morpholinocyclohexene, 7%<br>undecatrienes[e], 9%<br>4-ethyl-8-morpholino-3,6-nonadiene, 63%<br>morpholinoheptadecatrienes, 28% |
| 29 | 1-Bromo-2-methyl-1-propene | isoprene | HM | P(o-tol)$_3$ | 4 days | 2,6-dimethyl-1,3,5-heptatriene, 12%<br>2,6-dimethyl-1-morpholino-2,5-heptadiene, 54%<br>2,6-dimethyl-3-morpholino-1,5-heptadiene, 8% |

[a]Reactants: 10 mmol. vinylic halide, 12.5 mmol. diene, 30 mmol. amine, one mole percent palladium acetate and two mole percent phosphine based on the halide (or a 5 or 10 time multiple of these ratios was used).
[b]HM = morpholine, HP - piperidine.
[c]Reactants: 20 mmol. vinyl bromide, 60 mmol. E-pentadiene, 50 mmol. morpholine, 1% palladium acetate and 2% tri-o-tolylphosphine.
[d]6% Tri-o-tolylphosphine used.
[e]Structures not established other than by molecular weights (HRMS).

In elaboration:

EXAMPLE 19 (supra)

Vinyl bromide, E-1,3-pentadiene, and morpholine reacted with one mole percent palladium acetate - two mole percent tri-o-tolylphosphine as catalyst in 17 hrs. at 100° C. to form 6-morpholino-1,4-heptadiene in 52% yield. (All yields hereinafter reported, except where otherwise noted, are of purified, isolated products.) In this instance a 3:1 ratio of diene to vinylic halide was used, it being found that better yields were obtained thereby than with the lower 1.25:1 ratio. The remainder of the product was polymer and higher boiling materials which were not identified.

The formation of the product in the above reaction can be readily explained on the basis of an addition of the vinyl-palladium intermediate to the terminal double bond of the diene followed by cyclization to the pi-allylic complex and a final attack of the amine upon the complex with displacement of the palladium-phosphine-halide group. The palladium then undergoes loss of halide ion and oxidatively adds more vinyl bromide to start the cycle again.

In contrast to the formation of the pi-allylic complex by a palladium hydride elimination-reverse readdition in the vinylic halide-olefin reaction, in the conjugated diene reaction the pi-allylic complex is formed directly from the initial adduct. It is also notable that the attack of the amine upon the pi-allylic complex is very selective, in that the product appears to be entirely the 6-morpholino adduct and little, if any, of the possible 4-adduct seems to be formed.

EXAMPLE 20 (supra)

In a much slower reaction than Example 19, Z-1-bromopropene, isoprene and morpholine gave 2-methyl-1-morpholino-2,5-heptadiene in 40% yield along with higher boiling unidentified products and polymers. The major point of interest in this Example was to determine whether or not the stereochemistry of the Z-1-bromopropene was retained in the product. The product appeared homogeneous by GLC (gas liquid chromatography) and NMR (nuclear magnetic resonance); however, IR (infrared) showed bands characteristic of both cis and trans olefinic groups. Therefore, the product may be a mixture of isomers. Aside from the stereochemistry with respect to the double bonds, the structure can be assigned conclusively from the NMR spectrum. The addition of the 1-propenyl group, therefore, was completely regio-selective, adding to the terminal

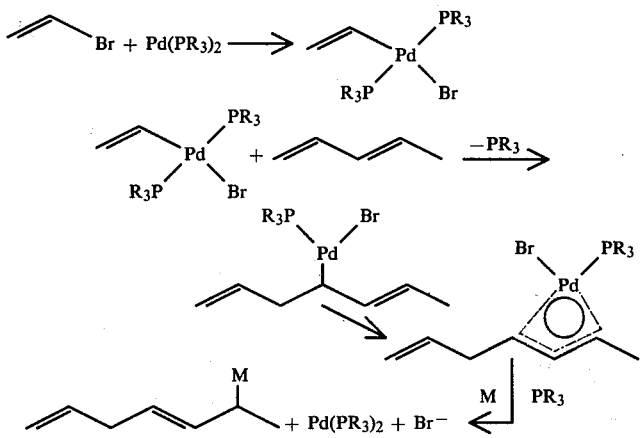

carbon of the less-substituted double bond of the isoprene. This contrasts with the mixture of positional isomers obtained when this halide was added to 1-hexene (refer Example 4, supra).

EXAMPLES 21–23, inclusive (supra)

2-Bromopropene reacted as expected from the foregoing results with 1,3-butadiene, isoprene and E-1,3-pentadiene giving amine adducts as the sole or predominant products in 40–60% yields. When piperidine was used as the amine, no triarylphosphine was required.

EXAMPLES 24 and 25

The reaction of 2-bromopropene with 4-methyl-1,3-pentadiene was more complex than Examples 20–23. The intermediate piallylic complex to be expected from this reaction, I infra, would have a gem dimethyl group on one of the pi-allylic carbons. Few complexes with this structure are known. The 1,1-dimethyl-pi-allylpalladium chloride phosphine derivatives are known. (Refer J. Powell and B. L. Shaw, *J. Chem. Soc. A,* 1967, 1839.) Structural studies revealed that carbon bearing the gem dimethyl group is trans to the phosphine, and less strongly bonded to the palladium than the primary allylic carbon. It is perhaps not surprising, therefore, to find products from the 4-methyl-1,3-pentadiene reaction arising from both the pi-complex expected to be formed directly, I infra, and the product produced by a palladium hydride elimination and reverse readdition, III infra. The product from the direct complex, II, was obtained in 26% yield (GLC), and the product from the rearranged complex, IV, in 3% yield. There was also produced 12% of conjugated triene, V.

gave the expected triene, VI infra, (39%), another isomer triene (13%), and 4-isopropenyl-1-methyl-3-piperidinocyclohexene, VII infra, (9%). The latter adduct is not the N-tertiary-alkylpiperidine derivative that might have been expected on the basis of the results obtained with the 4-methyl-1,3-pentadiene but rather the compound from attack of the amine at the secondary pi-allylic carbon. The difference is apparently due to the more bulky tertiary group in the cyclic compound. The N-t-butylpiperidine structure is hindered, and the situation apparently becomes significantly worse if the group is larger that t-butyl.

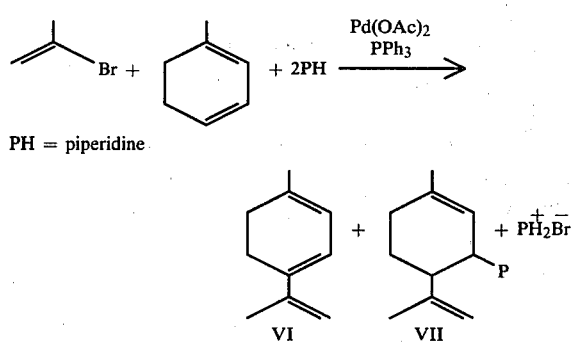

PH = piperidine

Morpholine reacted similarly to piperidine in this reaction.

EXAMPLE 28

A reaction between Z-3-iodo-3-hexene, morpholine and E-1, 3-pentadiene gave 9% trienes and 63% of the expected adduct, 4-ethyl-8-morpholino-3,6-nonadiene.

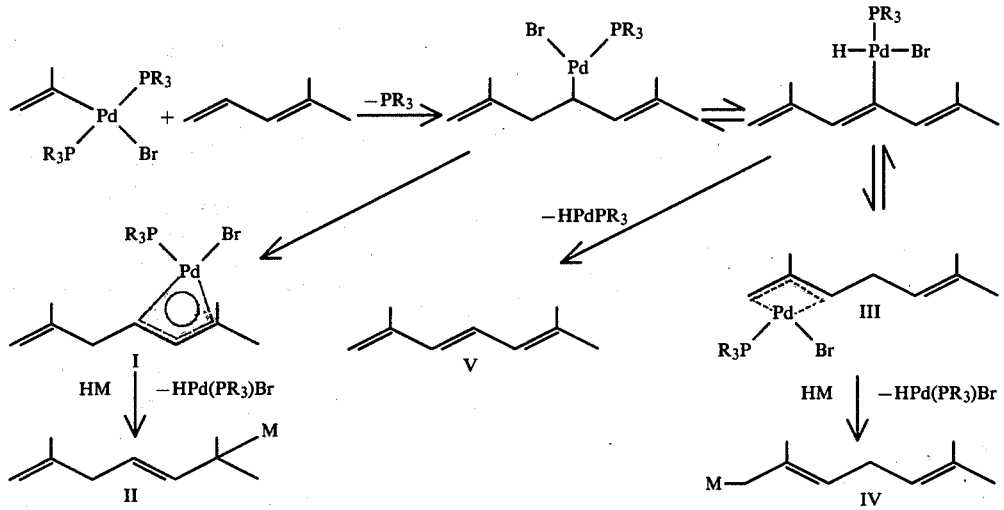

2-Bromopropene was also reacted with two cyclic olefins, 1,3-cyclo-hexadiene and 1-methyl-1,3-cyclohexadiene respectively. In Example 24, the first diene gave 21% conjugated triene and a 2:1 mixture of the two piperidine adducts (35% and 15%) resulting from attack at both ends of the presumed pi-allylic intermediate. Very probably the amine attacks trans to the side of the ring with the isopropenyl group and there is not a large difference in the environments around the two terminal allylic carbons in this compound.

EXAMPLES 26 and 27

In Example 26, the reaction of 1-methyl-1,3-cyclohexadiene with 2-bromopropene and piperidine

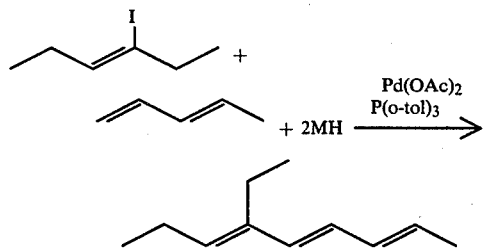

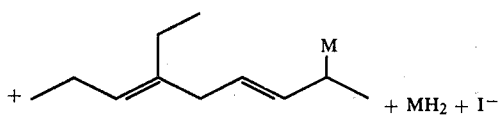

Qualitatively, Z-3-bromo-3-hexene and E-1,3-pentadiene gave the same products in approximately the same ratios as the iodo compound, but at a slower rate (30 hrs. required).

EXAMPLE 29

In this Example, 1-bromo-2-methyl-1-propene was reacted with morpholine and isoprene. This bromide added significantly in both directions to 1-hexene (refer Example 5), but only terminal addition of the alkyl group was obtained in the reaction with isoprene, although two allylic amine adducts were seen in a ratio of 54% terminal to 8% internal.

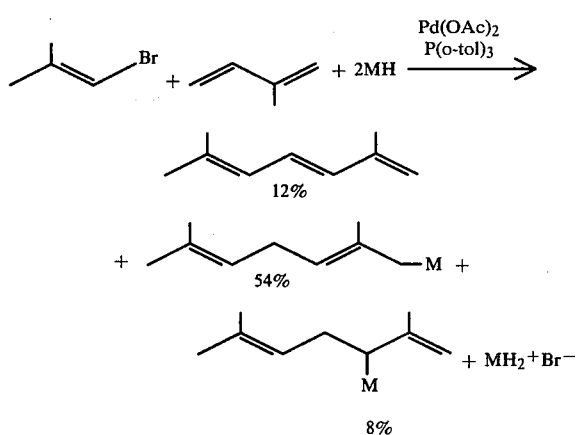

The morpholine adducts in this example can be converted into monoterpenes by adding one carbon atom. This was accomplished by first reacting the mixture with methyl chloroformate to give the chloride in 77% yield, and then carbonylating the chloride with carbon monoxide and ethanol using a palladium chloride catalyst. This latter reaction gave only a 40% yield of an E and Z mixture of ethyl 3,7-dimethyl-3,6- octadienoate. Treatment of this diene mixture with sodium ethoxide slowly isomerized it to ethyl geranate.

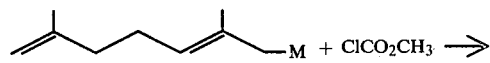

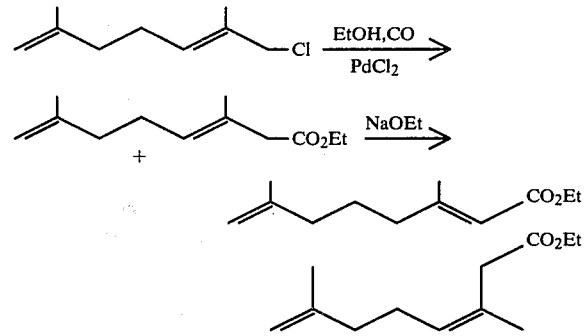

From the foregoing, it is seen that the palladium catalyzed reaction of vinylic halides with conjugated dienes and a secondary amine which produces tertiary 2,5-dienylamines is quite general. Yields are moderate to good, considering the specificity and complexity of the reaction. Finally, the reaction is of considerable synthetic value, since the tertiary amine group can be readily removed by known methods.

As many apparently widely different embodiments of this invention may be made without departing from the spirit and scope therof, it is to be understood that this invention is not limited to the specific embodiments thereof except as defined in the appended claims.

I claim:

1. The catalytic process of producing tertiary allylic amines from vinylic halides, with up to about 30 carbon atoms, which comprises reacting said halide with a mono-, di-, or tri-substituted ethylene, or ethylene itself with an unhindered basic secondary amine, in the presence of a palladium catalyst.

2. The process of claim 1 in which the reaction is carried out at a temperature within the range of from 50° to 150° and at a pressure of 0.5 to 50 atmospheres.

3. The process of claim 1 wherein the palladium catalyst is a palladium(II) salt of one of the group consisting of acetate and chloride.

4. The process of claim 1 wherein the palladium catalyst is a triarylphosphine complex which is either added as the compound per se or wherein said complex is formed under the existing reaction conditions by adding a palladium(II) salt and the triarylphosphine.

5. The process of claim 2 wherein said vinylic halides are bromides and said catalyst is palladium chloride.

6. The process of claim 5 wherein said catalyst is composed of a palladium(II) salt and two equivalents of one of the group consisting of tri-o-tolylphosphine and triphenylphosphine.

7. The process of claim 2 in which 3-bromo-1-propene is reacted with an acrolein acetal and a basic secondary amine.

8. The process of claim 2 in which 9-decen-1-ol is reacted with vinyl bromide and a basic secondary amine.

* * * * *